United States Patent [19]
Wagner, Jr.

[11] 3,939,263
[45] Feb. 17, 1976

[54] METHODS OF COMBATTING INSECTS AND ACARINA USING OXYGENATED DERIVATIVES OF S-(TERT-BULYTHIO)METHYL O,O-DIETHYL PHOSPHORODITHIOATE AND PHOSPHOROTHIOATE

[75] Inventor: Frank Albert Wagner, Jr., Pennington, N.J.

[73] Assignee: American Cyanamid Company, Stamford, Conn.

[22] Filed: Dec. 19, 1974

[21] Appl. No.: 534,381

Related U.S. Application Data

[62] Division of Ser. No. 358,756, May 9, 1973, Pat. No. 3,878,267.

[52] U.S. Cl. ............ 424/216; 260/985; 424/DIG. 8

[51] Int. Cl.$^2$............................................. A01N 9/36
[58] Field of Search........................ 424/216, DIG. 8

[56] References Cited
UNITED STATES PATENTS

| | | | |
|---|---|---|---|
| 2,952,700 | 9/1960 | Lorenz et al........................ | 260/948 |
| 2,963,505 | 12/1960 | Muhlmann et al.................. | 260/948 |
| 3,408,426 | 10/1968 | Yamamoto et al. ................ | 260/948 |

*Primary Examiner*—Stanley J. Friedman
*Assistant Examiner*—Allen J. Robinson
*Attorney, Agent, or Firm*—H. G. Jackson

[57] ABSTRACT

The invention also relates to a method for controlling insects and acarina with the oxygenated derivatives of S-(tert-butylthio)methyl O,O-diethyl phosphorodithioate and phosphorothioate.

6 Claims, No Drawings

METHODS OF COMBATTING INSECTS AND ACARINA USING OXYGENATED DERIVATIVES OF S-(TERT-BULYTHIO)METHYL O,O-DIETHYL PHOSPHORODITHIOATE AND PHOSPHOROTHIOATE

This is a division of application Ser. No. 358,756 filed May 9, 1973, now U.S. Pat. No. 3,878,267 issued Apr. 15, 1975.

BACKGROUND OF THE INVENTION

1. Field of the Invention

The invention pertains to novel chemicals useful as pesticides.

2. Description of the Prior Art

Japanese Pat. No. 9297/66 teaches a method of preparing compounds of the formula:

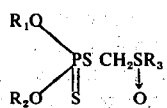

and their use as insecticides. Other patents of interest are U.S. Pat. Nos. 2,596,076 (1952) and 3,408,426 (1968). I have discovered that the compound O,O-diethyl S-(tert-butylsulfonyl)methyl phosphorodithioate is much less toxic to mammals (mice) than the art compound O,O-diethyl S-(tert-butylsulfinyl)methyl phosphorodithioate, and exhibits insecticidal activity equal to, and in some cases superior to, this art compound.

SUMMARY OF THE INVENTION

The invention relates to novel compounds having the structure:

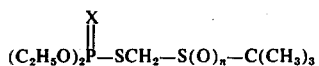

wherein x is sulfur or oxygen and $n$ is an integer 1 or 2; with the proviso that when $n$ is 1 X is oxygen. The invention includes the compounds O,O-diethyl S-(tert-butylsulfonyl)methyl phosphorothioate, O,O-diethyl S-(tert-butylsulfonyl)methyl phosphorodithioate and O,O-diethyl S-(tertbutylsulfinyl)methyl phosphorothioate. The invention also relates to methods for the preparation of the compounds and to a method for controlling insects and acarina therewith by contacting the pests with an insecticidally or acaricidally effective amount of a compound of the above-identified structure. The invention further relates to a method for protecting crops from attack by insects and acarina by applying an acaricidally or insecticidally effective amount of a compound having the above structure to the foliage of the crops or to the soil in which the crops are grown.

DESCRIPTION OF THE PREFERRED EMBODIMENTS

The sulfoxide of O,O-diethyl S-(tert-butylthio)methyl phosphorothioate is prepared by reacting this ester with a 5 to 10% excess of sodium meta-periodate at ambient temperature. The reaction is preferably carried out in an aqueous system with initial mixture of the reactants at about 0° to 10°C. O,O-Diethyl S-(tert-butylthio)methyl phosphorothioate can also be converted to the corresponding sulfone by reaction of the phosphorothioate with two equivalents of m-chloroperbenzoic acid. The reaction is preferably carried out at a low temperature, i.e., 0° to 10°C. followed by a period at ambient temperature in a low boiling solvent such as methylene chloride.

Conversion of O,O-diethyl S-(tert-butylthio)methyl phosphorodithioate to the corresponding sulfone can be achieved by the reaction of said phosphorodithioate with potassium permanganate in aqueous tert-butyl alcohol using magnesium sulfate as a buffer, or by reaction with two equivalents of m-chloroperbenzoic acid in a solvent such as methylene chloride.

The compounds of the invention are highly effective insecticidal and acaricidal agents. They may be applied with conventional type applicators as contact, soil or systemic insecticides and acaricides and may be used in combination with a wide variety of adjuvants and formulation aids. They may be advantageously employed with the use of either solid or liquid adjuvants in the form of granular formulations, wettable powders, emulsifiable concentrates, dusts and dust concentrates. They may also be employed neat or in combination with about 5 to 50% by weight of a high aromatic diluent having a mixed aniline point of about 30° to 95°F., aromatic content between 60 and 100%, flash point above 125°F. and specific gravity between 0.880 and 1.5 at 60°/60°. Among the diluents useful in the latter formulations are Panasol AN-5, Socal 44-L, Esso HAN, high aromatic solvent code DMN, light cycle oil and the like. These low volume and ultra-low volume compositions are generally applied with hand or aerial equipment designed to disperse said compositions as finely divided droplets having a mass median diameter between about 25 and 150 microns.

With the conventional type formulations as described above, the active ingredient may be initially formulated with a concentrated composition, comprising the active ingredient in a solid or liquid adjuvant which serves as a formulation aid or conditioning agent, permitting the concentrates to be further mixed with a suitable solid or liquid carrier.

Useful liquid adjuvants in which the toxicant is dissolved, suspended or distributed include, for example, xylene, benzene, lower alcohols $C_1$–$C_4$, fuel oil or the like, with or without an emulsifying agent. For application, the resulting solution can be further diluted with either water or an organic diluent, such as deodorized kerosene. Concentrations in the range of from about 5 to about 95% are generally suitable for initial solution. When diluted for application, suitable solutions may contain the active ingredient in concentrations of from about 0.5 to about 5000 ppm.

Suitable solid adjuvants include, for example, attapulgite, kaolin, talc or diatomaceous earth in granular or finely ground form. The active ingredient can be conveniently formulated with the solid adjuvants as dusts, dust concentrates, wettable powders, granulars and the like.

Dusts are generally prepared by mixing together from about 1 to 10% by weight of the active ingredient with a finely divided inert diluent such as attapulgite, kaolin, diatomaceous earth, talc or fuller's earth. These formulations can then be applied with dusting equipment to the foliage of agronomic crops or fields, meadows, forests, or the like, which are to be protected from insect attack or where insect control is desired. Application is generally sufficient to provide between about 0.125 pound and 8 pounds per acre of active material.

Dust concentrates are usually prepared in the same manner as dusts, but generally from about 25 to 75% by weight of the active compound and from 75 to 25% by weight of diluent are used.

Wettable powders are prepared in the same fashion as the dust concentrates; however, from about 1 to 5% by weight of an emulsifying agent and from about 1 to 5% by weight of a dispersing agent are usually included in such formulations. Polyethylene glycols, methoxy polyethylene glycols, sodium lignosulfonate, calcium dodecylbenzene sulfonate, and the like, are among the emulsifying agents and dispersing agents which can be used in these formulations. In practice, the wettable powders are generally dispersed in water and applied as a dilute spray to the vegetation, soil or habitat where insect control is desired.

Excellent insect control and plant protection in fields, forests, crop lands, and the like, is generally achieved by application of the active ingredient at rates of from about 0.25 pound to about 8 pounds per acre.

The invention is further illustrated by the following examples which are not to be taken as limitative thereof. In these examples, the expression "TLC" refers to thinlayer chromatographic analysis on silica gel sorbent.

EXAMPLE 1

Preparation of O,O-diethyl S-(tert-butylsulfonyl)methyl Phosphorothioate

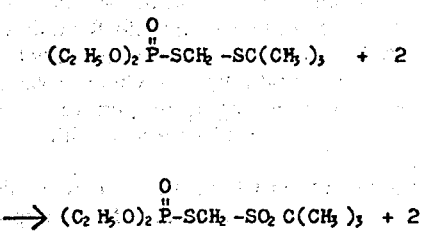

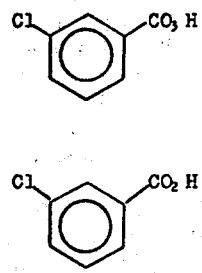

To a solution of O,O-diethyl S-(tert-butylthio)methyl phosphorothioate (13.6 grams, 0.050 mole) in 100 ml. of methylene chloride, cooled to 0° to 5°C., is added the solid m-chloroperoxybenzoic acid (20.4 grams of about 85% purity, 17.3 grams real, 0.10 mole) during 1 hour; the temperature of the exothermic reaction is maintained at 5° to 10°C. during the addition with external cooling. The reaction mixture is stirred for several minutes at ca. 5°C., allowed to warm, and then stirred at room temperature overnight. The mixture is filtered and the filtrate is washed with 50 ml. 2N NaOH, 25 ml. 2N NaOH, two 25-ml. portions of saturated NaCl and dried (MgSO$_4$). Reduced-pressure evaporation of the solvent from the dried solution gives 14.0 grams (91.9%) of moderately viscous, straw-colored liquid; TLC shows the presence of only trace amounts of contaminants. The reaction product has the following analysis.

Analysis Calculated for $C_9H_{21}O_5PS_2$: C, 35.51; H, 6.95; P, 10.18. Found: C, 35.29; H, 7.00; P, 10.37.

EXAMPLE 2

Preparation of O,O-diethyl S-(tert-butylsulfonyl)methyl Phosphorodithioate

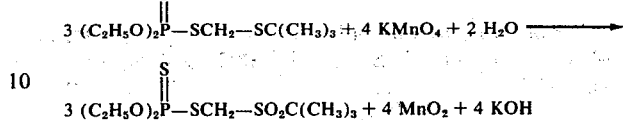

To O,O-diethyl S-(tert-butylthio)methyl phosphorodithioate (28.8 grams, 0.10 mole, ca. 94% pure) in 100 ml. of tert-butyl alcohol is added a solution of magnesium sulfate (12.0 grams, 0.100 mole, 50% excess) in 100 ml. of water. Solid potassium permanganate (21.1 grams, 0.133 mole) is added in portions to the stirred mixture during one hour; the temperature of the mildly exothermic reaction is maintained at 25° to 35°C. with external cooling. The reaction mixture is stirred at room temperature overnight. The mixture is suction-filtered and the insoluble paste washed with 300 ml. of methylene chloride. The water-butanol-methylene chloride filtrate is separated and the aqueous phase extracted with two 50 ml. portions of methylene chloride. The organic solutions are combined, dried (MgSO$_4$) and the solvents removed under reduced pressure to give 27.7 grams (86.7%) of moderately viscous, faintly straw-colored liquid. A 2.25-inch i.d. chromatographic column is filled to a height of 21 inches with 60/100 mesh Florisil, in carbon tetrachloride, the reaction product is placed on the column, and thirteen 1000-ml. effluent fractions are taken, using the following eluant series in 1000-ml. portions: CCl$_4$ (X2), 5% (vol.) CH$_2$Cl$_2$/CCl$_4$, 10% CH$_2$Cl$_2$/CCl$_4$, 15% CH$_2$Cl$_2$/CCl$_4$, 25% CH$_2$Cl$_2$/CCl$_4$, 50% CH$_2$Cl$_2$/CCl$_4$, 75% CH$_2$Cl$_2$/CCl$_4$, CH$_2$Cl$_2$ (X2) and CH$_3$OH (X3). The fractions are analyzed by TLC and fractions 9 (CH$_2$Cl$_2$ eluant), 10 (CH$_2$Cl$_2$ eluant), and 11 (CH$_3$OH eluant) are found to be single component. These fractions are combined and the solvents removed under reduced pressure to give 9.91 grams (31.0%) of viscous, straw-colored liquid with the following analysis.

Analysis Calculated for $C_9H_{21}O_4PS_3$: C, 33.75; H, 6.61; P, 9.67. Found: C, 33.60; H, 6.59; P, 9.80.

EXAMPLE 3

Preparation of O,O-diethyl S-(tert-butylsulfinyl)methyl Phosphorothioate

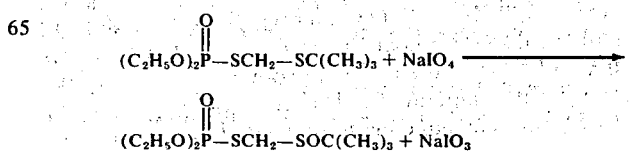

To a suspension of sodium periodate (11.8 grams, 0.055 mole, 10% excess) in 115 ml. of water, cooled to 0° to 5°C., is added O,O-diethyl S-(tert-butylthio)-methyl phosphorothioate (13.6 grams, 0.050 mole) and 5.0 ml. of methanol. The reaction mixture, in an ice bath contained in an insulated bucket, is stirred overnight, during which time the ice melts and the mixture attains room temperature. Fifty ml. of methylene chloride is stirred into the mixture and the solids are filtered and washed with an additional 50 ml. of methylene chloride. The filtrate is separated and the aqueous phase extracted with two 50-ml. portions of methylene chloride. The organic solutions are combined, washed with 25-ml. portions of saturated NaCl, 5% KOH, and saturated NaCl (X2), and then dried (MgSO$_4$). Reduced-pressure evaporation of the solvent from the dried solution gives 13.9 grams (96.5%) of clear, colorless oil which slowly crystallizes, melting point 34.5° to 36.0°C. Attempts to effect recrystallization are not successful. TLC shows the presence of only a trace amount of a contaminant.

Analysis Calculated for $C_9H_{21}O_4PS_2$: C, 37.48; H, 7.34; P, 10.74. Found: C, 37.78 and 37.60; H, 7.19 and 7.29; P, 10.61.

EXAMPLE 4

The insecticidal and acaricidal activity of the compounds of the invention is demonstrated in the following tests.

The procedures employed are reported below and followed by data obtained which are presented in Table I.

Procedures

Tarnished Plant Bug — *Lygus Lineolaris* (Palisot de Beauvois)

A cotton plant with two true leaves expanded is dipped for 3 seconds with agitation in a 35/65% water-/acetone mixture containing 100 ppm. of test compound and set in the hood to dry. One leaf is removed and placed in an 8-ounce waxed cup containing a wet 2-inch dental wick and 10 adult tarnished plant bugs, and a clear plastic lid is snapped on. After 2 days at 80°F., 50% r.h., mortality counts are made.

Cotton Boll Weevil — *Anthonomus grandis* Boheman

A cotton plant with cotyledons expanded is dipped for 3 seconds with agitation in 35/65% aqueous acetone mixture containing 100 ppm. of test compound and set in the hood to dry. One cotyledon is removed from the plant and placed in a 4-inch petri dish containing a moist filter paper on the bottom and 10 adult weevils. After 2 days at 80°F., and 50% r.h., mortality counts are made, prodding each insect to distinguish dead ones from those "playing dead."

Two-Spotted Spider Mite — *Tetranychus urticae* (Koch)

Sieva lima bean plants, with primary leaves 3 to 4 inches long, are infested with about 100 adult mites per leaf 4 hours before use in this test, in order to allow egg-laying before treatment. The infested plants are dipped for 3 seconds with agitation into a 35/65% water/acetone mixture containing 1000 ppm. of test compound and the plants set in the hood to dry. After 2 days at 80°F., and 50% r.h., the adult mite mortality is estimated on one leaf under a 10X stereoscopic microscope. The other leaf is left on the plant an additional 5 days and then examined at 10X power to estimate the kill of eggs and of newly hatched nymphs, giving a measure of ovicidal and residual action, respectively.

Southern Armyworm — *Spodoptera eridania* (Cramer)

A Sieva lima bean plant with just the primary leaves expanded to 3 to 4 inches is dipped for 3 seconds with agitation in a 35/65% water/acetone mixture containing 1000 ppm. of test compound and set in the hood to dry. Following this, one leaf is placed in a 4-inch petri dish which has a moist filter paper in the bottom and ten third-instar armyworm larvae about three-eighths inch long. The dish is covered and held at 80°F., and 50% r.h. After 2 days, mortality counts and estimates of the amount of feeding are made. Compounds showing partial kill and/or inhibition of feeding are held for an extra day for further observations.

Mexican Bean Beetle — *Epilachna varivestis* Mulsant

Sieva lima bean plants (two per pot) with primary leaves 3 to 4 inches long, are dipped in a 35/65% water/acetone mixture containing 100 ppm. of test compound and set in the hood to dry. One leaf is removed from a plant and placed in a 4-inch petri dish containing a moist filter paper on the bottom and 10 last-instar larvae (13 days from hatching). The day after treatment, another leaf is removed from the plant and fed to the larvae after removing the remains of the original leaf. Two days after treatment, the third leaf is fed to the larvae, this usually being the last needed. The fourth leaf is used on the third day after treatment if the larvae have not finished feeding. The test is now set aside and held until adults have emerged, usually in about nine days after treatment began. After emergence is complete, each dish is examined for dead larvae, pupae or adults; deformed pupae or adults; larval-pupal intermediates or pupal-adult intermediates; or any other interference with normal molting, transformation and emergence of pupae or adults.

Soil Insecticide

Southern Corn Rootworm — *Diabrotica undecimpunctata howardi* Barber

Initial Test: 25 ml. aliquots of air-dry-treated potting soil (containing 100 ppm. of test compound) are placed in 2-ounce wide-mouth screw-top glass jars. Twelve and one-half milliliters of Littleton silt loam soil and 1 milliliter of millet seed (food for larvae) are added, the jars capped and the contents thoroughly mixed about 2 minutes on a rotary tumbler. Each jar then receives 5 ml. of tap water and ten southern corn rootworm larvae (*Diabrotica undecimpunctata howardi* Barber) 6 to 8 days old. The jars are loosely capped and placed in the holding room at 26.7°C. and 60% r.h. with constant light. Mortality counts are made after 6 days. Corrected percent mortality data is recorded on standard forms.

Soil Systemic Insecticide Tests

Corn and cotton seed (three seeds each) are planted in treated soil (containing about 100 ppm. of the compound). Thirty milliliters of treated soil are placed in a peat container 5 × 5 × 5.5 cm., and three seeds each of corn and cotton planted. The containers are filled with an additional 30 ml. of treated soil. The treatments are removed to the greenhouse maintained about 26°C. without supplementary light. Water is supplied as needed. After three weeks, foliage of the corn is clipped and placed in glass petri dishes (90 mm. × 10 mm.) with moist filter (9 cm. Whatman No. 1) paper and ten third-instar southern armyworm (*Spodoptera eridania* Cramer) larvae about 8 mm. long. The dishes are covered and placed in the holding room with constant light at 26.7°C. and 60% r.h. for 2 days, when mortality counts are made.

The cotyledonary leaves of the cotton are clipped after three weeks and placed in glass petri dishes (90 mm. × 10 mm.) with moist filter (9 cm. Whatman No. 1) paper and ten adult boll weevils (*Anthonomus grandis* Boheman). The dishes are covered, placed in the holding room with constant light at 26.7°C. and 60% r.h. for 2 days, when mortality counts are made.

Western Potato Leafhopper — *Empoasca abrupta* Say

A Sieva lima bean plant with the primary leaf expanded to 3 to 4 inches is dipped into a 35/65% water-/acetone mixture containing 100 ppm. of test compound and set in the hood to dry. A 1-inch piece of the tip of one leaf is cut off and placed in a 4-inch petri dish with a moist filter paper in the bottom. From three to 10 second-instar nymphs are tapped from the culture plants into the test dish and rapidly covered. Mortality counts are made after 2 days at 80°F., and 50% r.h.

Malaria Mosquito — *Anopheles quadrimaculatus* Say — Adult Test

Ten ppm. acetone solutions of test compounds are poured into wide-mouth 2-ounce jars each containing a microscope slide. The slides are removed from the test solution with forceps and laid horizontally to dry on a wide-mouth 4-ounce bottle. When dry, they are placed in the same 4-ounce bottle and 10 4-to 5-day-old mosquitoes of mixed sexes are added to each bottle. A piece of cotton gauze held on by an elastic band serves as a lid and wad of cotton soaked in 10% honey solution serves as food. Mortality counts are made after one day at 80°F., 50% r.h.

Bean Aphid — *Aphis fabae* Scopoli

Two-inch fiber pots, each containing a nasturtium plant 2 inches high and infested with 100 to 150 aphids 2 days earlier are placed on a 4 RPM turntable and sprayed with a 35/65% water/acetone mixture containing 100 ppm. of test compound for two revolutions with an Atomizer at 20 psi. air pressure. The spray tip is held about 6 inches from the plants and the spray directed so as to give complete coverage of the aphids and the plants. The sprayed plants are laid on their sides on white enamel trays. Mortality estimates are made after one day at 70°F., 50% r.h.

Housefly — *Musca domestica* Linneaus

Groups of 25 adult female houseflies three to 5 days old are lightly anesthetized with $CO_2$, placed in wide-mouthed pint mason jars, and covered with a screen cap. The test compound is a 100 ppm. 35/65% water-/acetone solution. Two milliliters of this is pipetted into a 10-dram vial and diluted to 40 ml. with 10% sugar solution, giving a final concentration of 5 ppm. in sugar water. The mouth of the vial is covered with a single layer of cheesecloth, inverted and placed on the screen cap of the fly jar, so that the flies can feed on the solution through the screen. Mortality counts are made after 1 day and 3 days at 80°F., 50% r.h.

Ticks — *Boophilus microplus*

The efficacy of the compounds of the present invention for controlling ticks is demonstrated by the following tests against United States *Boophilus microplus* ticks.

In these tests, 20 larvae are enclosed in a pipette sealed at one end with a gauze material. A 10% acetone/water solution with the drug in it is then sucked through the pipette with a vacuum hose, thus simulating a spray system. The ticks are then held for 48 hours and mortality is determined. Data are reported below.

TABLE I

| Structure | Insecticidal and Acaricidal Activity of Test Compounds % Kill | | | | | | | | | Soil Insecticide | | |
|---|---|---|---|---|---|---|---|---|---|---|---|---|
| | Tarnished Plant Bug ppm. | Cotton Boll Weevil ppm. | Two-Spotted Spider Mite ppm. | | Southern Armyworm ppm. | | Mexican Bean Beetle ppm. | | Southern Corn Rootworm ppm. | | |
| | 100 | 100 | 1000 | 100 | 1000 | 100 | 100 | 10 | 100 | 10 | 1 |
| $(C_2H_5O)_2\overset{S}{\underset{\|}{P}}-SCH_2-\overset{O}{\underset{\overset{\|}{O}}{\underset{\|}{S}}}-C(CH_3)_3$ | 100 | 90 | 100 | 100 | 100 | 100 | 100 | — | 100 | 100 | 100 |
| $(C_2H_5O)_2\overset{O}{\underset{\|}{P}}-SCH_2-\overset{O}{\underset{\overset{\|}{O}}{\underset{\|}{S}}}-C(CH_3)_3$ | 100 | 90 | 100 | 100 | 100 | 100 | 100 | 100 | 100 | 100 | 61 |
| $(C_2H_5O)_2\overset{O}{\underset{\|}{P}}-SCH_2-\overset{O}{\underset{\overset{\|}{O}}{\underset{\|}{S}}}-C(CH_3)_3$ | 100 | 90 | 100 | 100 | 100 | 100 | 90 | 70 | 100 | 100 | 0 |
| $(C_2H_5O)_2\overset{S}{\underset{\|}{P}}-SCH_2-\overset{O}{\underset{\overset{\|}{O}}{\underset{\|}{S}}}-C(CH_3)_3$ (Art) | 100 | 100 | 100 | 100 | 100 | 70 | 90 | 80 | 100 | 100 | 95 |

| Structure | Systemic Insecticide | | | | Western Potato Leaf-Hopper ppm. | | Malaria Mosquito ppm. | | Bean Aphid ppm. | | House-fly ppm. | Ticks ppm. |
|---|---|---|---|---|---|---|---|---|---|---|---|---|
| | Southern Armyworm ppm. | | Cotton Boll Weevil ppm. | | | | | | | | | |
| | 100 | 10 | 100 | 10 | 100 | 10 | 10 | 1 | 100 | 10 | 1 | 5 | 100 | 33 |
| $(C_2H_5O)_2\overset{S}{\underset{\|}{P}}-SCH_2-\overset{O}{\underset{\overset{\|}{O}}{\underset{\|}{S}}}-C(CH_3)_3$ | 0 | | 90 | | — | | 100 | 50 | 100 | 100 | 100 | 100 | — | — |

TABLE I-continued

| Structure | Southern Armyworm ppm. | | Systemic Insecticide Cotton Boll Weevil ppm. | | Western Potato Leaf-Hopper ppm. | | Malaria Mosquito ppm. | | Bean Aphid ppm. | | House-fly ppm. | Ticks ppm. | |
|---|---|---|---|---|---|---|---|---|---|---|---|---|---|
| | 100 | 10 | 100 | 10 | 100 | 10 | 10 | 1 | 100 | 10 | 1 | 5 | 100 | 33 |
| $(C_2H_5O)_2\overset{O}{\underset{\|}{P}}-SCH_2-\overset{O}{\underset{\|}{S}}-C(CH_3)_3$ | 100 | 100 | 100 | 100 | 100 | 40 | 100 | 100 | 100 | 100 | 100 | — | | |
| $(C_2H_5O)_2\overset{O}{\underset{\|}{P}}-SCH_2-\overset{O}{\underset{\underset{O}{\|}}{S}}-C(CH_3)_3$ | 100 | 100 | 100 | 100 | 50 | 0 | 100 | 100 | 100 | 100 | — | 0 | | |
| $(C_2H_5O)_2\overset{S}{\underset{\|}{P}}-SCH_2-\overset{O}{\underset{\|}{S}}-C(CH_3)_3$ (Art) | 100 | 100 | 100 | 100 | 80 | 0 | 100 | 100 | 100 | 100 | — | 0 | | |

EXAMPLE 7

Mammalian toxicity data for the compounds of the invention are given in Table II, below. For the tests reported in Table II, 20 male albino mice of the CFI strain, weighing approximately 18 grams to 20 grams are selected. The phosphates are readied for administration by preparing a solution or dispersion in corn oil (Mazola), the concentration of which is adjusted so that the total volume of the dose is 0.5 ml./kg. in every case. The initial solution is prepared by deciding upon the maximum dosage in mg./kg. to be administered and preparing 10 ml. of this solution of such a concentration that the desired dosage in mg./kg. is delivered when 0.5 ml. of the solution is administered for 20 grams of mouse body weight. Serial dilutions differing by a factor of two are then prepared for each lower dosage level. LD$_{50}$ stands for the lethal dose in mg./kg. which kills 50% of the mice.

TABLE II

| | LD$_{50}$ |
|---|---|
| $(C_2H_5O)_2\overset{S}{\underset{\|}{P}}-SCH_2-\overset{O}{\underset{\|}{S}}-C(CH_3)_3$ (Art) | 3.4 |
| $(C_2H_5O)_2\overset{O}{\underset{\|}{P}}-SCH_2-\overset{O}{\underset{\underset{O}{\|}}{S}}-C(CH_3)_3$ | 3.4 |
| $(C_2H_5O)_2\overset{S}{\underset{\|}{P}}-SCH_2-\overset{O}{\underset{\underset{O}{\|}}{S}}-C(CH_3)_3$ | 14.0 |
| $(C_2H_5O)_2\overset{O}{\underset{\|}{P}}-SCH_2-\overset{O}{\underset{\|}{S}}-C(CH_3)_3$ | 1.1 |

I claim:

1. A method for the control of insects and acarina, comprising contacting said insects and acarina with an insecticidally or acaricidally effective amount of a compound of the structure:

$$(C_2H_5O)_2\overset{X}{\underset{\|}{P}}-SCH_2-S(O)_n-C(CH_3)_3$$

where X is sulfur or oxygen and $n$ is 1 or 2; with the proviso that when $n$ is 1, X is oxygen.

2. The method of claim 1 wherein the compound is O,O-diethyl S-(tert-butylsulfonyl)methyl phosphorothioate.

3. A method for protecting crops from attack by insects and acarina, comprising applying to said crops or the soil in which they are grown an insecticidally or acaricidally effective amount of a compound having the structure:

$$(C_2H_5O)_2\overset{X}{\underset{\|}{P}}-SCH_2-S(O)_n-C(CH_3)_3$$

where X is sulfur or oxygen and $n$ is 1 or 2; with the proviso that when $n$ is 1, X is oxygen.

4. The method of claim 3 wherein the compound is O,O-diethyl S-(tert-butylsulfonyl)methyl phosphorodithioate.

5. A method for the control of soil-borne insects, comprising applying an insecticidally effective amount of a compound of the structure:

$$(C_2H_5O)_2\overset{X}{\underset{\|}{P}}-SCH_2-S(O)_n-C(CH_3)_3$$

where X is sulfur or oxygen, and $n$ is 1 or 2; with the proviso that when $n$ is 1, X is oxygen, to soil inhabitated by said insects.

6. The method of claim 5 wherein the compound is O,O-diethyl S-(tert-butylsulfonyl)methyl phosphorodithioate.

* * * * *